United States Patent
Weinhold

(10) Patent No.: US 7,227,648 B2
(45) Date of Patent: Jun. 5, 2007

(54) METHOD AND APPARATUS FOR A TOUCH-FREE EXAMINATION OF OBJECTS, PARTICULARLY REGARDING THE SURFACE CHARACTER OF THE SAME

(76) Inventor: Wolfgang Weinhold, Haugerring 6, 97070 Würzburg (DE)

( * ) Notice: Subject to any disclaimer, the term of this patent is extended or adjusted under 35 U.S.C. 154(b) by 375 days.

(21) Appl. No.: 10/477,344

(22) PCT Filed: May 8, 2002

(86) PCT No.: PCT/DE02/01667

§ 371 (c)(1),
(2), (4) Date: Jun. 7, 2004

(87) PCT Pub. No.: WO02/090952

PCT Pub. Date: Nov. 14, 2002

(65) Prior Publication Data

US 2004/0233421 A1    Nov. 25, 2004

(30) Foreign Application Priority Data

May 8, 2001   (DE) .............................. 101 22 313

(51) Int. Cl.
*G01B 11/14* (2006.01)
*F21V 13/00* (2006.01)
(52) U.S. Cl. .................. 356/601; 356/623; 250/208.1; 362/33
(58) Field of Classification Search ........ 356/601–625, 356/326, 328, 330–334, 445–448, 425; 362/33, 362/252; 250/208.1, 234–235, 559.32, 557
See application file for complete search history.

(56) References Cited

U.S. PATENT DOCUMENTS

| 5,416,590 | A | * | 5/1995 | Stover et al. ................ 356/623 |
| 5,524,163 | A | * | 6/1996 | Kobayashi et al. ........... 385/96 |
| 5,671,084 | A | * | 9/1997 | Kurtz .......................... 359/362 |
| 5,686,720 | A | * | 11/1997 | Tullis ....................... 250/208.1 |
| 5,963,333 | A | * | 10/1999 | Walowit et al. ............. 356/425 |
| 6,424,416 | B1 | * | 7/2002 | Gross et al. ................ 356/326 |
| 6,547,409 | B2 | * | 4/2003 | Kiest et al. .................... 362/33 |

* cited by examiner

Primary Examiner—Sang H. Nguyen
(74) Attorney, Agent, or Firm—Edwin D. Schindler

(57) ABSTRACT

A method and apparatus for optically examining an object in a contactless manner, in which light successively impinges upon the surface of an object being examined. The different sources of light strike the object surface at different angles of incidence and reflect off the surface and are then able to be measured by an image sensor which produces a plurality of image data sets having different contents. In this way, a first image data set is produced with the incident light from which form-independent or non-topographical characteristics, such as color errors, can be derived. Form-dependent or topographical characteristics, such as scratches, are derived from a second image data set formed with glancing light or oblique light. Before the form characteristics are derived from the first image data set, it is essential that the distorting influences of form-independent characteristics are eliminated from the first image data set via the second image data set. Furthermore, the apparatus is embodied as a portable manual apparatus, which is placed by hand, in an approximately light-permeable manner, on the surface of the fixed object, or is displaced in contact with the surface.

19 Claims, 2 Drawing Sheets

Figure 4:
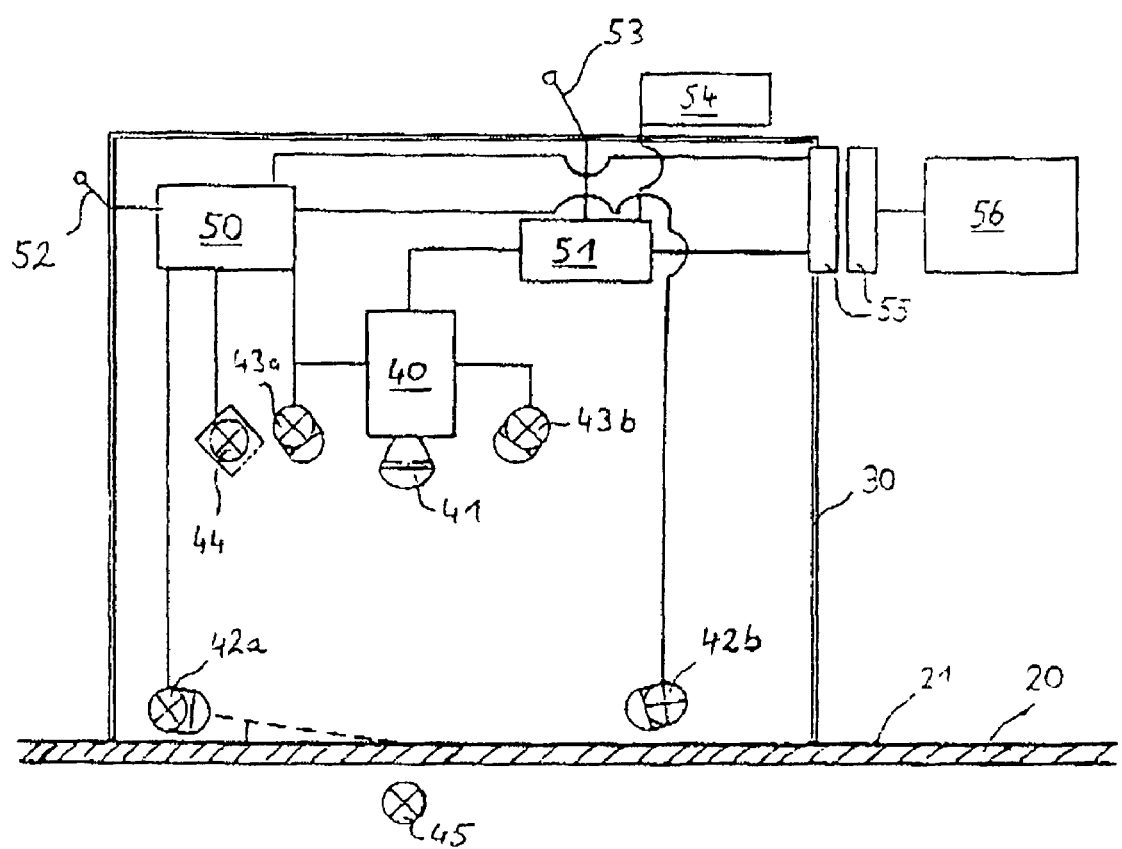

Fig. 1
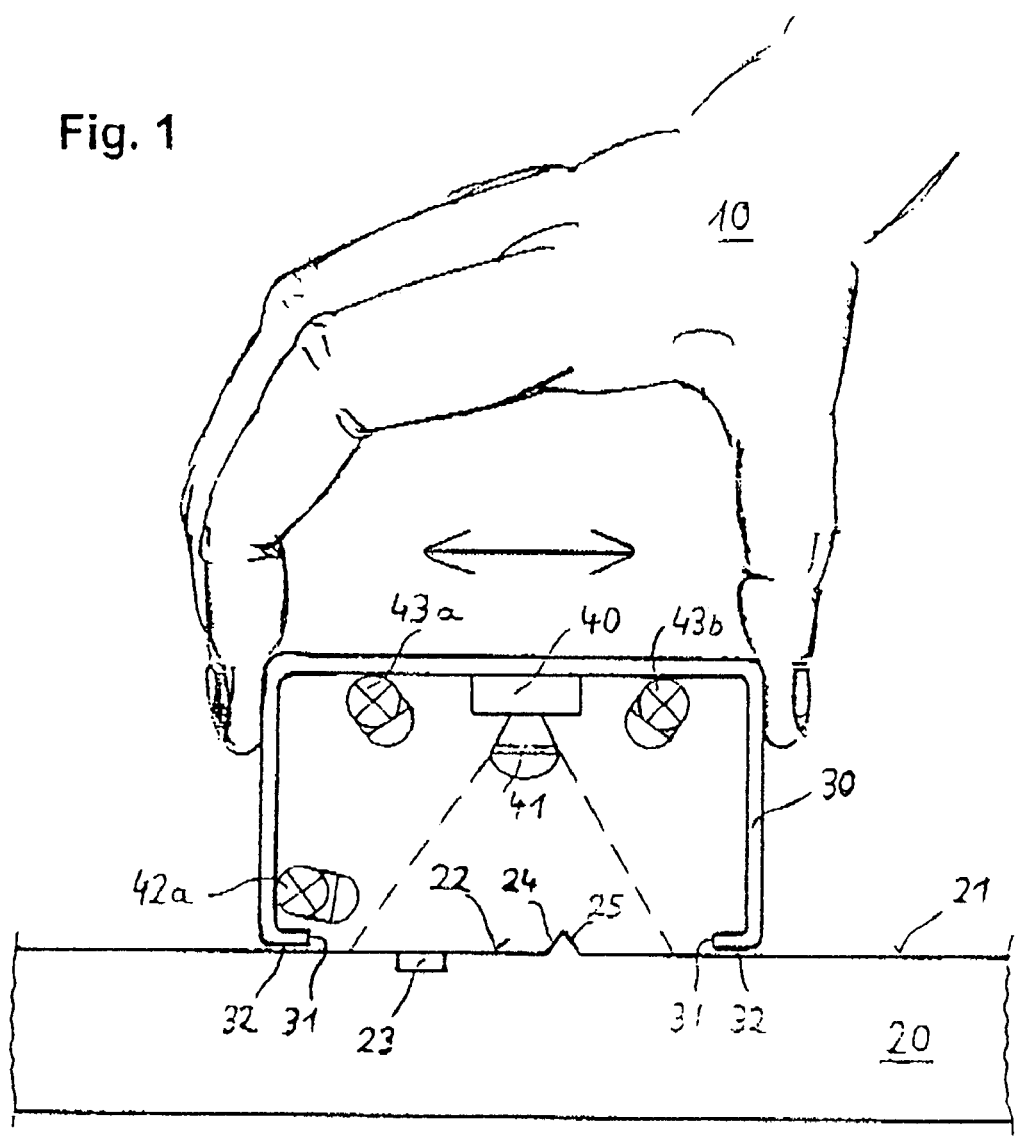
Fig. 2
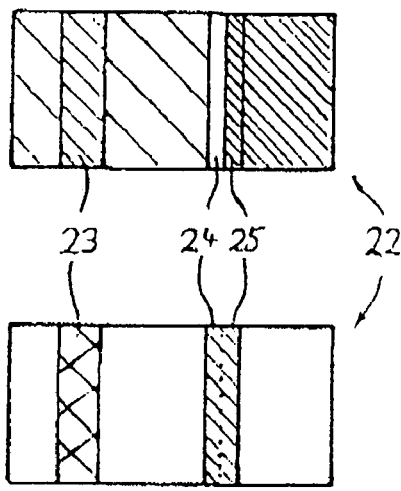
Fig. 3

METHOD AND APPARATUS FOR A TOUCH-FREE EXAMINATION OF OBJECTS, PARTICULARLY REGARDING THE SURFACE CHARACTER OF THE SAME

BACKGROUND OF THE INVENTION

1. Technical Field of the Invention

The present invention relates to a procedure and apparatus for touch-free examinations of objects, especially regarding their surface character.

2. Description of the Prior Art

Procedures and appliances, employing a touch-free technique to examine the surface character with the aid of optical resources are already existing. Surfaces may be illuminated using rays of light or oblique light to illuminate the surface from a flat or oblique angle, simply by localising and quantifying superjacent soil particles, unevenness, rough spots, processing traces etc. This relies on the fact that depending on the specification of such deviations compared to the target surface character, more or less intense bright/dark spots can build up i.e. due to illuminated and shaded edges, which in turn allows to draw conclusions about the three-dimensional surface character.

This proceeding is adequately known under the term ray of light or oblique light procedure, i.e. DE 197 16 264 A1. In reverse it is also used in a simplified manner for the production of topographic maps in order to provide a flat map with the impression of a plastic landscape with the help of an imaginary incidence of light. The desired effect is also known as shading or shadow plastic. Generally speaking there is a functional relationship between the angle of incidence, the three-dimensional orientation and the position of the sub-area, especially its inclination, height and the angle of emergence of reflected light. The reflected light is recorded as gray scale information with the means of an opto-electronic sensor primarily vertically inclined to the surface, i.e. a line or matrix sensor, and then transferred to digital image processing. This procedure is particularly well-suited for punctual, linear or frequently re-occuring surface deviations, such as soiling and scratches for example.

A strip light procedure projecting a geometrically defined pattern (for example bright and dark strips) with the help of a light source onto the surface of an object is also known. Depending on the specification of surface elevations and depressions, the projected pattern is deformed. For example, on a sub-area more exposed to the light source, strip width and distance are reduced. On the other hand, on a sub-area less exposed to the light source, i.e. a depression, width and distance are increased. A three-dimensional surface model may be derived from the pattern's deformation via suitable algorithms, after the reflected light has also been gathered with an opto-electronic sensor and its readings have been transferred to digital processing analysis. This procedure (also known from the DE 197 30 885 A1), which is also called coded light or projection procedure, is particularly well suited if a detailed surface structure with a corresponding light/dark contrast range is non-existent—for example on a smooth surface with large-area curvatures. Depending on the surface character, the emitted light of the light source is reflected from the surface by both the rays of light and the strip light procedure. The brightness and gray scale dispersion, which is being gathered by an image sensor, correlates more or less closely with this surface character.

However, these well-known procedures and appliances show a disadvantage: They can only supply three-dimensional surface features i.e. geometrical surface data of the object. Moreover the functional correlation between brightness dispersion and surface character only strictly apply to a surface with constant material qualities. The measurement result may turn out to be false when the surface combines various adjacent materials with different photometric or shape-independent features such as reflection, transmission and absorption parameters. This means that an overlap in the desired brightness dispersion of the above mentioned procedure occurs in case of surface character deviations with brightness data of multicolored, patterned or mottled surface segments that do not deviate from the target surface character, which complicates the assignment of the resulting brightness data to a distinct shape (for example an edge with an x incline) or a distinct material (for example soiling of the surface independent and material specific gray tone y).

The DE 198 39 882 includes a lighting system for color matching of coated car body surfaces intending to obtain surface features on the one hand and surface independent features on the other hand (for example material specific parameters such as chrominance errors) through differently arranged and implemented light sources. There is a differentiation between a basic lighting set, which hits the car body surface at a 45-degree angle of incidence and which is used as a working light for repairs and the detection of chrominance and polishing errors, and a structural light set with special implemented linear light sources that also emit at a 45 degree angle and helps to detect surface deformations, i.e. dents. Vehicles to be examined are directed through the large and stationary light set where mechanics do repair jobs and work on manual color matching of the car body surface. It becomes complicated, however, when a person needs to change the perspective in order to detect the different types of errors and is therefore no longer able to check one and the same surface segment. If the person wants to check the same surface segment for both types of errors he/she has to choose another position. Moreover this method only allows the assessment of either non-topographical types of errors (i.e. soiling or chrominance errors) or topographical types of errors (i.e. dents). A combined assessment is not possible. This may be compared to replacing visual observation with a camera a person is using instead. Altogether this procedure appears difficult and complex in its implementation and is only practical for glossy surfaces. The dimensions of the lighting set only facilitate its stationary operation.

In addition, the DE 35 40 228 A1 includes a description and a procedure for the implementation of controls for soldering points which works like this: From various angles of incidence, light is directed at the soldering points of a pcb and the reflected light from the soldering point is gathered by one or more B/W image sensors. This way, a majority of images with various informational content, depending on the angle of incidence, is generated. The accuracy of the soldering point structure may then be assessed with the help of a computational synthesis of the images. The reason for a decision (after the shape-independent characteristics have already been generated) whether (only if a distinct shape of the soldering point could not be assessed) there is a spot of minor solder, a circuit without solder or pcb material is the way in which the combination of shape characteristics or shape-independent characteristics is taking place—whereby the examination is always based on the same material.

A combined data processing for the reduction of shape-independent impacts of errors is not planned at this point.

The arrangement itself consists of a stationary housing in which several light sources are set up to emit at various angles towards the soldering point. The housing is also equipped with a lighting aperture directed at the soldering point as well as a second aperture through which several cameras can gather the light reflected by the soldering point. The mobile pcb with soldering points arranged on the X/Y table is underneath the housing or its lighting aperture. This arrangement is disadvantageous as it is only used for stationary operation e.g. in a production line. Furthermore, just like with the housing's second aperture, the distance between the housing and the pcb is prone to extraneous light.

SUMMARY OF THE INVENTION

Therefore, the present invention of the above-mentioned procedure and appliance (i.e., apparatus) facilitates an easy and correct assessment of the surface character of an object, as well as the flexible coverage of various applications.

The objectives of the present invention are accomplished by the claimed method and apparatus, whereby in order to optically examine an object in a contactless manner, light which successively impinges upon the surface of an object being examined, strikes the object surface at different angles of incidence and reflects off the surface and is then able to be measured by an image sensor, which produces a plurality of image data sets having different contents. In this way, a first image data set is produced with the incident light from which form-independent or non-topographical characteristics, such as color errors, can be derived. Form-dependent or topographical characteristics, such as scratches, are derived from a second image data set formed with glancing light or oblique light. Before the form characteristics are derived from the first image data set, it is essential that the distorting influences of form-independent characteristics are eliminated from the first image data set via the second image data set. Furthermore, the apparatus is embodied as a portable manual apparatus, which is placed by hand, in an approximately light-permeable manner, on the surface of the fixed object, or is displaced in contact with the surface.

Accordingly, the appliance housing, which is equipped with several light sources and a light aperture, and the object face each other or take opposite positions. After that a light illuminates one of the objects's surface segments from various angles, and at least one image sensor gathers the emitted or reflected light, depending on the angle of incidence. Each angle of incidence and each image sensor produces at least one image data set of the surface segment. Shape features may be obtained from at least one first image data set and shape-independent features may be obtained from at least one second image data set. It is significant for the invention that a) operating personnel can hold the housing, put it on the surface nearly light-tightly and move it across the surface and that, b) before shape features are derived from the first image data set, the first image data set together with the second image data set is reduced by falsifying influences of shape-independent features.

As known from the state of the art, light source types are different, which means they all perform different tasks depending on the angle of incidence. According to the invention, light sources of a first type are directed at the surface as rays of light/oblique light, respectively at an oblique or flat angle of incidence. This way, surface character features may be derived from the reflected light, especially deviations from the target shape e.g. superjacent soil particles, processing traces, scratches or inhomogenities in general compared to an evenly structured target surface. The light sources of the second type are directed at the surface as incident or transmitted-light illumination respectively at an oblique to vertical angle of incidence. This way, the reflected or transmitted light can show shape-independent features, such as material density, color, moisture or temperature.

It is beneficial that the shape features derived from the first image data set and the optical appearance and the material specific features derived from the second image data set can be allocated with one single procedure and one single appliance for each surface segment. This means that the image data amount can be linked or correlated and this makes the assessment of each image data set considerably easier and more reliable. For example: The surface structure of printed paper, the so-called paper roughness as well as the print volume caused by the application of the printing ink can be analyzed seperately and correlated to the surface structure. This invented procedure and appliance particularly consider features of different materials (during or before the derivation of shape features) from the first image data set. The falsifying influence of an area printed in dark gray on a shape model to be derived by including the second image data set can be reduced or calibrated with the use of suitable algorithms. Only the second image data set distinctly shows that there is a dark area and an edge (Talflanke) not shadowed as it should be assumed from the first data set's exclusive assessment. Ideally of course, this calibration can also be carried out for multicolored, patterned, mottled surfaces, but also for surfaces with extremely weak color inhomogeneities not visible to the naked eye.

Another advantageous characteristic of this appliance is the housing's design as a hand apparatus. The personnel can place it directly or move it freely, preferably by hand, on or across any surface segments of the object. During an examination it is not necessary to lift the housing from an adjacent surface area and put it down again, which can be very inconvenient during large-scale examinations and which can also strain or misalign sensitive opto-electronic components. The object also does not need to be placed at or underneath the housing's light aperture, i.e. the bringing over a production line, in order to reach a mutual measurement or examination position because, according to the invention, the item is stationary. Full contact between the housing and the surface is also impossible here and, in contrast to the invented appliance, extraneous light is an additional problem. In the form of a very advantageous design the image sensor is already integrated in the housing of the appliance and the housing is therefore handy and compact. An additional advantage is that the distance between the image sensor and the surface segment to be examined stays constant and cannot be shifted by external impacts. Consequently, a separate autofocus or alignment function is not necessary. On top of that, the optical system of the housing's image sensor cannot get dirty or be damaged quite so easily. When the distance between the light source of a second type and the surface grows or stays the same, it facilitates another advantageous minimization of the housing. An even more compact design is possible when the light sources of the second type are arranged behind the image sensor. All of these measures allow a flexible and universal handling of the invented appliance. It can also be stored away or transported safely in a small equipment case. Here is another possibility: Instead of or supplementary to rays of light or an oblique light source, with the help of additional light sources of the first type, a geometrically defined pattern is projected onto the object's surface. A pinhole aperture corresponding with the pattern inside the light path is assigned to this additional light source. The quality of the evaluation result is increased by the calibration of the first image data set along with the backup of the second image data set. In addition, procedures should be considered where projected patterns of several strip lights positioned at varios spots are overlaid on the surface.

It proves to be particularly advantageous when an additional light source of a second type is assigned as a transmitted light source, which transmits light through an object into the housing. This light source of a second type is arranged outside the housing opposite of the object facing the image sensor, preferably at an angle of incidence vertical to the surface. As a result, transparent, translucent or perforated materials, e.g. paper or foil, can be examined. The transmitted light, on the other hand, is gathered by an image sensor and produces an additional second image data set from its readings. It is hereby particularly advantageous that the transmission conduct allows direct conclusions on the allocation of density, i.e. granularity of the paper's cellulose, and that this information can be combined with the first image data set. This means the effects of discontinuities within the material and potential deviation from the shape on the surface can be assessed in conjunction. The light arranged as an illumination through the object can be constructively connected to the remaining components of the appliance or preferably arranged in a separate way with constant distance from it. Such a light source can be installed stationary underneath the object to be examined in a testing line, e.g. as an illumination table with several of these light sources whereas the remaining components are installed mobile or also stationary in a housing above the object. A constructively and electrically independent transmitted light source may be controlled via a radio remote control—as long as it is not activated permanently.

It is advantageous that while considering the object to be examined and the purpose thereof, lots of different combinations of light sources of a first and second type are feasable, e.g. incident light with rays of light, incident light with strip light, incident light and transmitted light with rays of lights or incident light and transmitted light with strip light. Therefore procedure and application are particularly well suited for quality control in connection with target values of samples and for documentation purposes, e.g. for the production accompanying control of web materials or for the quality control of car body surfaces. Yet they can also be utilized in the medical sector, e.g. quantity, area and volume of skin moles may be monitored in periods of time.

The invented application includes an image sensor which can also be constructed as a single opto-electronic sensor, which scans the surface sequentially, for example, with a swinging or rotating mirror face or which can also be constructed as a line or preferably as a matrix sensor (like for example a commercial CCD camera). Preferably, a suited lens optic and an aperture unit are assigned to the image sensor. The image sensor is able to gather the light reflected or transmitted from the item directly or via appropriate redirection units such as beam-splitting prisms or deflection mirrors. Of course, several image sensors can be used simultaneously or sequentially—no matter if they are of the same or different types—and their image data can be combined. During the pixel and display element linking of the first and the second image data set it proves to be advantageous, however, to have these produced by the same image sensor. This way costly adjustment work is not required, which otherwise would become necessary in order to accurately overlap the image data set which normally doesn't succeed one hundred percent. Furthermore it is promising to use sensors for color and spectral analysis in order to clearly increase the informational content of the second image data set with regard to material specific features. The range of the image sensor in particular is not just limited to the visible area of the light.

The image sensor is arranged in a way to gather the light reflected or transmitted from the surface with its optical axis directly or via a redirection unit. The light is gathered at an angle of approx. 60 to 90 degrees to the surface, vertically if possible. The data is fed into or accessed from a control or analysis unit where the data can be turned into image data and sent to another, particularly a common analysis. The light sources used can be simple bulbs, discharge lamps or preferably semiconductor light sources, e.g. so-called LEDs. Those particularly have the advantage of producing different light spectra through accessing and can be used to analyze the object; Their narrow-band radiation pattern is also an advantage. Monochromatic light may also be used. Moreover, the spectrum of light sources is not limited to visible light. Preferably lens optical systems are assigned to the light sources. With the help of these systems a desired angle of radiation can be achieved. Especially the light sources of the first type show a narrow angle of radiation or no beam divergence at all. The form of the light sources can be in the form of ring illumination with reflected light and linear order of single light sources (e.g. LED row) with rays of light. Of course, the light sources can be single, arbitrarily combined or preferably arranged by type or depending on their angle of incidence turned on and off in sequence. An operating mode with permanent activation is conceivable whereas the light sources may be dimmed, i.e. regulated in their brightness. The angle of incidence of the light sources of the first type can be between 5 and 20 degrees, preferably 7 degrees, and the angle of incidence of the light sources of the second type between 45 and 90 degrees, preferably 60 degrees. If several light sources of the same type are installed, it can be of advantage that they radiate in different, preferably regular horizontal directions on the surface or are arranged around it. Light sources directed towards the object can be replaced accordingly and equally through combinations of redirection units, e.g. prisms, mirrors or light conductors, with other light sources, external ones for example. Preferably, these redirection units are portable, so that the light source type and the angle of incidence may be chosen freely.

Image sensor and light sources of the appliance as invented are connected to a control and/or analysis unit, which is preferably in the housing itself, and can be controlled by a keyboard unit or an operator via a display located on the outer side of the housing. The control and/or analysis unit can be connected by an interface to an external processing unit and exchange signals, especially image data. Image sensor and light sources are also connected to a power source, which is preferably located in the inner part of the housing. Power can also be supplied by the processing unit.

BRIEF DESCRIPTION OF THE DRAWING FIGURES

The invention is explained below using two design examples and referring to the figures in the drawing.

FIG. 1 a sectional view of the appliance as invented whose housing is placed onto an object by hand FIG. 2 a first set of image data of the object according to FIG. 1

FIG. 3 a second set of image data of the object according to FIG. 1, and

FIG. 4 a schematic outline of the appliance

DETAILED DESCRIPTION OF THE DRAWING FIGURES AND PREFERRED EMBODIMENTS

In FIG. 1 you can see a hand 10 touching the readily available housing 30 of the invented appliance with its fingers. As clearly shown with a double arrow, the housing 30 can be laterally displaced by hand 10 obverse surface 21 of a fixed object 20 after it was laid or put on the object. Housing 30 lies with its contact areas 32 roughly light tight on surface 21, i.e. through the light aperture, which is planned between the edges 31, so that no extraneous light can get into in inner part of the housing 30.

In the interior of housing 30 an image sensor 40 is attached on the housing top side. This sensor's optic axis is essentially directed vertically to surface 21. An optical system with the light aperture unit 41 is assigned to image sensor 40. The dashed lines between the optical system with aperture unit 41 and surface 21 show the image angle of image sensor 40 and also limit the surface segment 22 recorded by it, see FIG. 1 and 2. On both sides of image sensor 40 there are two light sources of the second type 43a and 43b connected at the inner housing top side. It is visible that they are directed towards surface 21 under an angle of incidence of approx. 50 degrees, i.e. these light sources fulfill the function of an incident illumination, if possible, producing a picture which appears natural to the human eye.

In addition a source of light of the first type 42a is firmly arranged at the left lower edge of housing 30 and with an angle of incidence of approx. 6 degrees directed towards surface 21, i.e. this light source fulfills the function of rays of light, which facilitates the perception of three-dimensional shape characteristics in the form of light/dark fields. Optics are upstream to light sources 43a, 43b and 42a respectively, which give their angle of reflected beam, whereby light sources 43a and 43b exhibit a broader angle of reflected beam than light source 42a. With light source 42a, as intended as ray of light, a particularly narrow angle of reflected beam is desirable. Surface 21, in the region of surface segment 22, includes foreign material 23 with photometric characteristics deviating from the other part of surface 21, such as another color for example or other shape-independent characteristics. Furthermore surface 21, likewise within the range of surface segment 22, exhibits an elevation with a first edge 24, turned towards light source 42a, and a second edge 25, turned away from light source 42a. For the execution of the procedure as invented the light source of the first and second type are successsively switched on by type, whereas the light respectively reflected from surface segment 22, here without any other deflection units, is gathered by image sensor 40 and a first and respectively second image data set is produced.

In FIG. 2 and FIG. 3 the first and the second image data set is shown, just like it was produced by image sensor 40 by surface segment 22 by using the light sources of the first and second type mentioned under FIG. 1., i.e. FIG. 2 shows the image data set for the ray of light and FIG. 3 shows the image data set for the incident light. The various hatchings represent different gray tones, and the following applies:The denser the hatching, the darker the gray tone. From FIG. 2 it is therefore evident that edge 24 turned towards light source 42a is the brightest area while edge 24 is strongly inclined and was illuminated nearly at a vertical angle, and edge 25 turned away from light source 42a is the darkest area, as it was completely shaded by the elevation. As expected, the areas on both sides of foreign material 23 have the same low gray tone, as these even parts of surface segment 22 were illuminated using the same angle of incidence. Foreign material 23 has a material-specific, only partially expressive gray tone. If attempts are made now to derive shape characteristics of surface segment 22 exclusively based on this first image data set, the pertinent shape parameters for the area of foreign material 23 as well as for the area next to edge 25b will turn out to be wrong. The pertinent gray tones of these areas are darker than the gray tones of the other even areas on both sides of foreign material 23 are darker, therefore misleadingly indicate a medium to strong inclination in these areas. Computational consideration of the second image data set under FIG. 3 for the derivation of shape parameters from the first image data set pursuant to FIG. 2, may reduce the misleading impact. For example, compared to the remaining surface segment 21, foreign material 23 in the second image data set is seen in a different color, see cross hatching. With the help of this information, the color influence in the first image data set can be "filtered" before deriving any shape parameters. Edges 24 and 25 are equally dark, they exhibit, however, the same color as surface segment 22. This information confirms the assumption from the first image data set that this actually involves an elevation with two edges. In addition, it is conceivable that light sources 43a and 43b are successively activated and two different second image date sets are produced, from which the elevation with edges 24 and 25 in the form of a stereo image may then be derived.

Finally, FIG. 4 schematically shows a block diagram of the invented appliance. Just like under FIG. 1, housing 30 of the appliance rests on surface 21 of the object, this way covering part of surface 21. On the inside of housing 30, on the other hand, an image sensor 40 with optics and lens unit 41 will be centered above surface 21. Furthermore, just like under FIG. 1, two light sources of the second type 43a and 43b and one light source of the first type 42a are designed. In addition, another light source across from it of the first type 42b is layed out in housing 20 on the left. The light sources of the first type 42a and 42b are close to surface 21 and reflect a small or respectively flat angle of incidence on it. Supplementary and besides light source 43a, this design example has a light source of the first type designed as strip light source 44, which can project a geometrically defined pattern onto surface 21. From the deformation of the pattern the shape of surface 21 may be derived. Finally, on the side of object 20 opposite image sensor 40 a light source of the second type 45 is designed. In case object 20 is translucent or perforated, it is able to screen it in the direction of image sensor 40. In this design example, light source 45 is constructively and electrically separate from the other parts of the appliance. All light sources located in housing 8 as well as the image sensor are connected through wires not specified in more detail with a control/analysis unit 50 an an internal power supply 51. The various light sources may be turned on and off via a first switch 52—individually, together or by type. With the help of a second switch 53, the power supply 53 or respectively all components supplied with power are turned on and off. Next to switch 53 a diplay and/or control unit is laid out. At the left wall of housing 30, an interface 55 is laid out in the upper area, connecting the control/analysis unit 50 and the internal power supply 51 with an external computer unit 56.

Referenced Symbols
10 hand
20 object
21 object surface
22 surface segment
23 foreign material
24 first edge of an elevation
25 second edge of an elevation
26 housing
31 edge of lighting aperture
32 bearing surface
40 image sensor
41 optics with lens unit
42a/b light sources, first type as strip light
43a/b light sources, second type as incident light
44 light source, first type as ray of light
45 light source, second type as transmitted light
50 control/analysis electronics
51 internal power supply
52 light source switch
53 power switch
54 operation unit/display
55 interface
56 computer unit

The invention claimed is:

1. A method for a non-contact examination of an object, comprising the steps of:
    positioning a housing containing a plurality of light sources therein with a lighting aperture in said housing for permitting light from said plurality of light sources to exit said housing toward an object to be examined, so that said plurality of light sources are capable of illuminating the object;
    successively illuminating a surface segment of the object to be examined by positioning the lighting aperture of said housing at several different angles of incidence;
    gathering light radiating from the surface segment of the object at each of said several different angles of incidence by at least one image sensor;
    producing at least one first image data set for each of said several different angles of incidence for each of said at least one image sensor for the surface segment of the object;
    deriving shape characteristics from said at least one first image data set;
    deriving shape-independent characteristics from at least one second image data set, so that with said second image data set, said at least one first image set is reduced by misleading impacts of said shape-independent characteristics before said shape characteristics from said at least one first image set are derived, the object to be examined being kept stationary and said housing being movable relative to the surface segment of the object.

2. The method for a non-contact examination of an object according to claim 1, wherein said step of deriving shape characteristics from said at least one first image data set and said step of deriving shape-independent characteristics from at least one second image data set utilize the same said image sensor.

3. The method for a non-contact examination of an object according to claim 1, wherein said step of deriving shape characteristics from said at least one first image data set is carried out by projecting a geometrically defined pattern of light onto the surface segment of the object to be examined.

4. The method for a non-contact examination of an object according to claim 1, wherein said step of deriving shape-independent characteristics from said at least one second image data set is carried out by transmitting light through the object to be examined.

5. Apparatus for a non-contact examination of an object, comprising:
    a housing containing a plurality of light sources therein and a lighting aperture for allowing exit of said plurality of light sources from said housing and directed toward a surface segment of an object to be examined, said housing being a portable hand device movable in opposition to the surface segment of the object;
    a first light source of said plurality of light sources within said housing being directed toward the surface segment of the object with an optical axis of said first light source being at an oblique to flat angle of incidence to the surface segment of the object;
    a second light source of said plurality of light sources within said housing being directed toward the surface segment of the object with an optical axis at an oblique to vertical angle of incidence to the surface segment of the object; and,
    means for controlling said first light source and said second light source within said housing, said means for controlling including at least one image sensor gathering light radiated from the surface segment of the object to be examined, said at least one image sensor being a color image sensor in said housing with a distance between said second light source placed in said housing and said surface segment being equal to, or greater than, a distance between said image sensor and said surface segment, and a control device connected with said first light source, said second light source and said at least one image sensor, said control device being within said housing.

6. The apparatus for a non-contact examination of an object according to claim 5, wherein said at least one image sensor is arranged within said housing so that said at least one image sensor is directly aligned with its optical axis at angle of 60° to 90° to the surface segment of the object to be examined.

7. The apparatus for a non-contact examination of an object according to claim 5, wherein said at least one image sensor is arranged within said housing so that said at least one image sensor is directly aligned over a deflection device at angle of 60° to 90° to the surface segment of the object to be examined.

8. The apparatus for a non-contact examination of an object according to claim 5, wherein said first light source is arranged at said angle of incidence to the surface segment of the object of 5° to 20° and said second light source is arranged at said angle of incidence to the surface segment of the object at 45° to 90° to the surface segment of the object.

9. The apparatus for a non-contact examination of an object according to claim 8, wherein said first light source is arranged at said angle of incidence to the surface segment of the object of 7°.

10. The apparatus for a non-contact examination of an object according to claim 8, wherein said second light source is arranged at said angle of incidence to the surface segment of the object of 60°.

11. The apparatus for a non-contact examination of an object according to claim 5, wherein said first light source and said second light source are each upstream of optics providing an angle of reflected beam.

12. The apparatus for a non-contact examination of an object according to claim 11, wherein said angle of reflected beam of said first light source is narrow or nearly zero.

13. The apparatus for a non-contact examination of an object according to claim 5, wherein said first light source is emitted onto the surface segment of the object at several horizontal directions.

14. The apparatus for a non-contact examination of an object according to claim 5, wherein said second light source is emitted onto the surface segment of the object at several horizontal directions.

15. The apparatus for a non-contact examination of an object according to claim 5, further comprising means for individually dimming said first light source and said second light source.

16. The apparatus for a non-contact examination of an object according to claim 5, wherein said first light source includes a lens aperture with a geometrically defined pattern.

17. The apparatus for a non-contact examination of an object according to claim 5, further comprising a power supply contained within said housing.

18. The apparatus for a non-contact examination of an object according to claim 5, further comprising a computer unit for supplying power.

19. The apparatus for a non-contact examination of an object according to claim 5, further comprising an interface allowing for an exchange of electric signals between said control device and an external computer unit.

* * * * *